US006892138B2

(12) United States Patent
Hashem et al.

(10) Patent No.: US 6,892,138 B2
(45) Date of Patent: May 10, 2005

(54) DETERMINING THE VISCOSITY OF A HYDROCARBON RESERVOIR FLUID

(75) Inventors: Mohamed Naguib Hashem, New Orleans, LA (US); Gustavo Antonio Ugueto, New Orleans, LA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/344,621

(22) PCT Filed: Jan. 17, 2002

(86) PCT No.: PCT/EP02/00519

§ 371 (c)(1),
(2), (4) Date: Feb. 12, 2003

(87) PCT Pub. No.: WO02/057597

PCT Pub. Date: Jul. 25, 2002

(65) Prior Publication Data

US 2003/0176973 A1 Sep. 18, 2003

Related U.S. Application Data

(60) Provisional application No. 60/302,982, filed on Jul. 3, 2001.

(30) Foreign Application Priority Data

Jan. 18, 2001 (EP) ......................................... 012001764

(51) Int. Cl.$^7$ ............................................... G01V 9/04
(52) U.S. Cl. ....................................................... 702/13
(58) Field of Search ................ 702/6, 9, 13; 73/152.24, 73/152.26, 152.55; 166/252.5; 250/256

(56) References Cited

U.S. PATENT DOCUMENTS 5,663,559 A * 9/1997 Auzerais et al. .......... 250/269.1
6,178,815 B1 * 1/2001 Felling et al. ............ 73/152.19
6,343,507 B1 * 2/2002 Felling et al. ............ 73/152.19

FOREIGN PATENT DOCUMENTS

EP          0 706 041        4/1996   .......... G01N/21/35

OTHER PUBLICATIONS

MN Hashem, et al., "Determination of Producible Hydrocarbon Type and Oil Quality in Wells with Synthetic Oil–Based Muds", SPE 39093, Oct. 5, 1997, pp. 353–366.
A Van Dusen, et al, "Determination of Hydrocarbon Properties by Optical Analysis During Wireline Fluid Sampling", SPE 63252, Oct. 1, 2000, pp. 1–13.
A Crombie, et al. << Innovations in Wireline Fluid Sampling:, Oilfield Review, 1998, pp. 26–41.
R Dorshow, "The Simultaneous Measurement of Interfacial Tension and Oil Viscosity at Reservoir Conditions for Prudhoe Bay Fluids by Surface Laser Light Scattering Spectroscopy", SPE 22633, 1995, pp. 120–128.

* cited by examiner

*Primary Examiner*—Donald McElheny, Jr.

(57) ABSTRACT

Determining the viscosity of a hydrocarbon reservoir fluid that is present in a formation layer traversed by a borehole, which method involves the steps of selecting a location in the formation layer; lowering in the borehole to the location a tool that has a central conduit having an inlet, means for displacing fluids through the central conduit, and an optical fluid analyzer; making an exclusive fluid communication between the formation and the inlet of the central conduit; obtaining a spectrum of the optical density; calculating a first factor that is the maximum optical density in a predetermined short-wavelength range multipled with the length of the short-wavelength range, calculating a second factor which is the integral over the same short-wavelength range of the spectrum, subtracting the second factor from the first factor to obtain a hydrocarbon oil property; and obtaining the magnitude of the in-situ viscosity from the oil property using a relation that has been obtained by fitting a curve through previously obtained data points having the measured magnitude of the actual viscosity as a function of the oil property.

6 Claims, 3 Drawing Sheets

DETERMINING THE VISCOSITY OF A HYDROCARBON RESERVOIR FLUID

PRIORITY CLAIM

The present application claims priority on European Application 01200176.4, filed on 17 Jan. 2001. It claims also the benefit of provisional applicaion Ser. No. 60/302,982 filed on Jul. 03, 2002.

FIELD OF THE INVENTION

The present invention relates to determining the viscosity of a hydrocarbon reservoir fluid.

BACKGROUND OF THE INVENTION

In order to measure the viscosity of a hydrocarbon reservoir fluid, a sample of the reservoir fluid is taken and analysed under reservoir pressure and temperature. A brief description of the way in which a PVT analysis is carried out is given in section 3 of the book Contributions in Petroleum Geology and Engineering, Volume 5, Properties of Oils and Natural Gases, K. S. Pederson et al, 1989. Such an analysis can be very accurate, however it takes a long time to be completed.

It is of great importance to know the viscosity of the reservoir fluid as soon as possible, preferably directly after a well has been drilled. Because, then there is still a possibility to adjust the design of the production and surface equipment to take into account the actual viscosity.

There are analysis tools, such as the modular dynamics formation tests from Schlumberger, the repeat dynamic tester from Halliburton and the reservoir characterization instrument from Western Atlas that are provided with an optical fluid analyser. Such an analyser operates by subjecting the fluid to be analysed to an absorption spectroscopy in the visible and near infrared ranges. The analyser measures the transmittance (which is the ratio of transmitted light energy to incident light energy) at different wavelengths. The output of the analyser is the optical density spectrum (which is the optical density, log(1/transmittance), as a function of wavelength).

Reference is made to SPE Paper 39093, Determination of producible hydrocarbon type and oil quality in wells drilled with synthetic oil-based muds, M. N. Hashem et al, 1997. In this paper it is disclosed that there is a correlation between the output of the analyser and the API gravity and between the output of the analyser and the gas-oil ratio.

Reference is further made to SPE paper 63252, Determination of hydrocarbon properties by optical analysis during wireline fluid sampling, A. van Dusen et al, 2000. This paper discloses that there is a correlation between the output of the analyser and some of the PVT properties, where PVT is an acronym used to refer to pressure, volume and temperature. According to this publication, density, saturation pressure, oil compressibility, formation volume factor and gas-oil ratio gave a good correlation, and that weaker correlations were found with other PVT properties.

SUMMARY OF THE INVENTION

Applicant has surprisingly found that there is a good correlation between the viscosity and a particular combination of the analyser output.

Thereto the method of determining the viscosity of a hydrocarbon reservoir fluid that is present in a formation layer traversed by a borehole according to the present invention comprises the steps of a) selecting a location in the formation layer;
b) lowering in the borehole to the location a tool that comprises a central conduit having an inlet, means for displacing fluids through the central conduit, and an optical fluid analyser;
c) making an exclusive fluid communication between the formation and the inlet of the central conduit;
d) obtaining a spectrum of the optical density;
e) calculating a first factor that is the maximum optical density in a predetermined short-wavelength range multiplied with the length of the short-wavelength range, calculating a second factor which is the integral over the same short-wavelength range of the spectrum, subtracting the second factor from the first factor to obtain a hydrocarbon oil property; and
f) obtaining the magnitude of the in situ viscosity from the oil property using a relation that had been obtained by fitting a curve through previously obtained data points comprising the measured magnitude of the actual viscosity as a function of the oil property.

Suitably the difference in step e) is divided by the optical density of the oil peak to obtain a crude oil property.

BRIEF DESCRIPTION OF THE DRAWINGS

The method will now be described by way of example in more detail with reference to the accompanying drawings, wherein.

DETAILED DESCRIPTION OF THE PREFERRED EMBODIMENT

Figure 1:
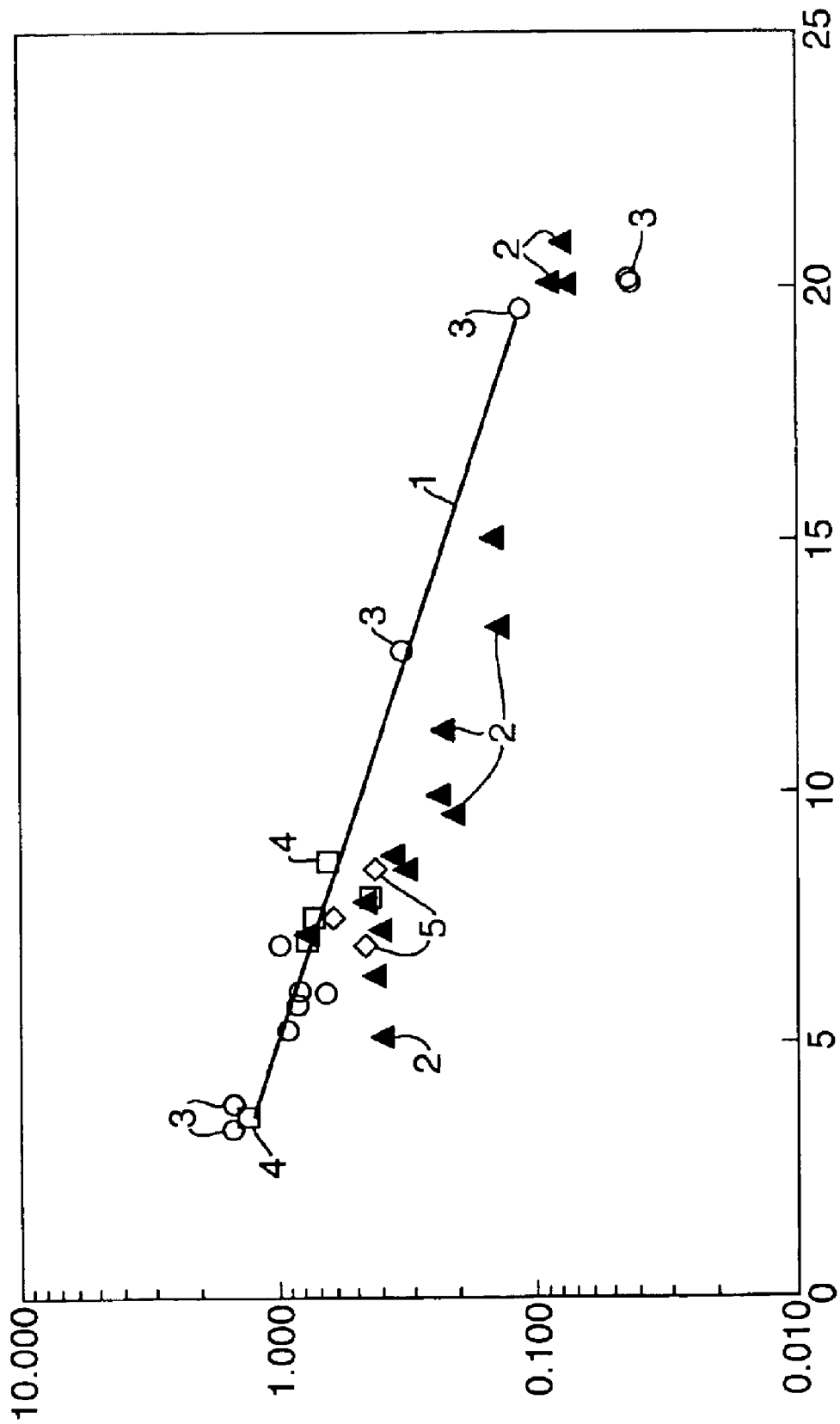
FIG. 1 shows the viscosity in centipoise (at in situ pressure and temperature) on the y-axis as a function of the hydrocarbon oil property on the x-axis in arbitrary units.

With reference to FIG. 1, we will now discuss the method of determining the viscosity according to the present invention in reverse order, wherein we start with discussing how the empirical relation is obtained.

The curve 1 shown in FIG. 1 shows the empirical relation that fits the data points 2, 3, 4 and 5 obtained from samples taken from reservoirs in the same geological area. For the sake of clarity, not all data points have been referred to with a reference numeral.

A data point was obtained as follows. At first a well was drilled to the formation layer of interest. Then a tool was lowered to the first of a set of locations in that formation layer. The tool comprises a central conduit having an inlet, means for displacing fluids through the central conduit, and an optical fluid analyser. At the location an exclusive fluid communication was made between the formation and the inlet of the central conduit by extending into the formation a probe having an outlet that is in direct fluid communication with the inlet of the central conduit. Then formation fluid was allowed to enter into the fluid receptacle and the spectrum of the optical density was obtained.

Then a first factor is calculated, which first factor is the maximum optical density in a predetermined short-wavelength range multiplied with the length of the short-wavelength range. Then a second factor is calculated, which second factor is the integral over the same short-wavelength range of the spectrum. Here the predetermined short-wavelength range is the visible light range. Then the second factor is subtracted from the first factor to obtain the hydrocarbon oil property, HOP.

Then a sample of the reservoir fluid was taken, and the viscosity of the sample was measured in a laboratory under reservoir conditions. And the measurements gave a data point in FIG. 1.

To get all data points these data were collected and analysed for more wells in the same geological area.

Then a curve was fitted through the data, and surprisingly, the data could be fitted with a considerable accuracy. The equation of the curve 1 is Visc=(2.164)exp(−0.15(HOP)), with a goodness of fit $R^2$ of 0.91, wherein $$R^2 = \frac{\left(\sum_{i=1}^{n}(x_i - x)(y_i - y)\right)^2}{\sum_{i=1}^{n}(x_i - x)^2 \sum_{i=1}^{n}(y_i - y)^2},$$

wherein n is the number of data points, $(x_1, \ldots, x_n)$ is the set of oil properties, x is the mean oil property, $(y_1, \ldots, y_n)$ is the set of measurements of the viscosity and y is the mean viscosity. $R^2$ is the squared value of the correlation coefficient.

We now discuss how the viscosity of an unknown hydrocarbon reservoir fluid that is present in a formation layer of interest traversed by a borehole is determined in situ.

At first a tool is lowered to the first of a set of locations in that formation layer. The tool comprises a central conduit having an inlet, means for displacing fluids through the central conduit, and an optical fluid analyser. At the location an exclusive fluid communication is made between the formation and the inlet of the central conduit by extending into the formation a probe having an outlet that is in direct fluid communication with the inlet of the central conduit. Then formation fluid is allowed to enter into the central conduit and a spectrum is obtained.

Then the optical density spectrum is used to calculate the hydrocarbon oil property, and the oil property is used with the empirical relation to get the viscosity that is required.

Suitably, the crude oil property is used, this is the hydrocarbon oil property divided by the optical density of the oil peak. The oil peak is the optical density at a wavelength of about 1 700 nanometer.

Figure 2:
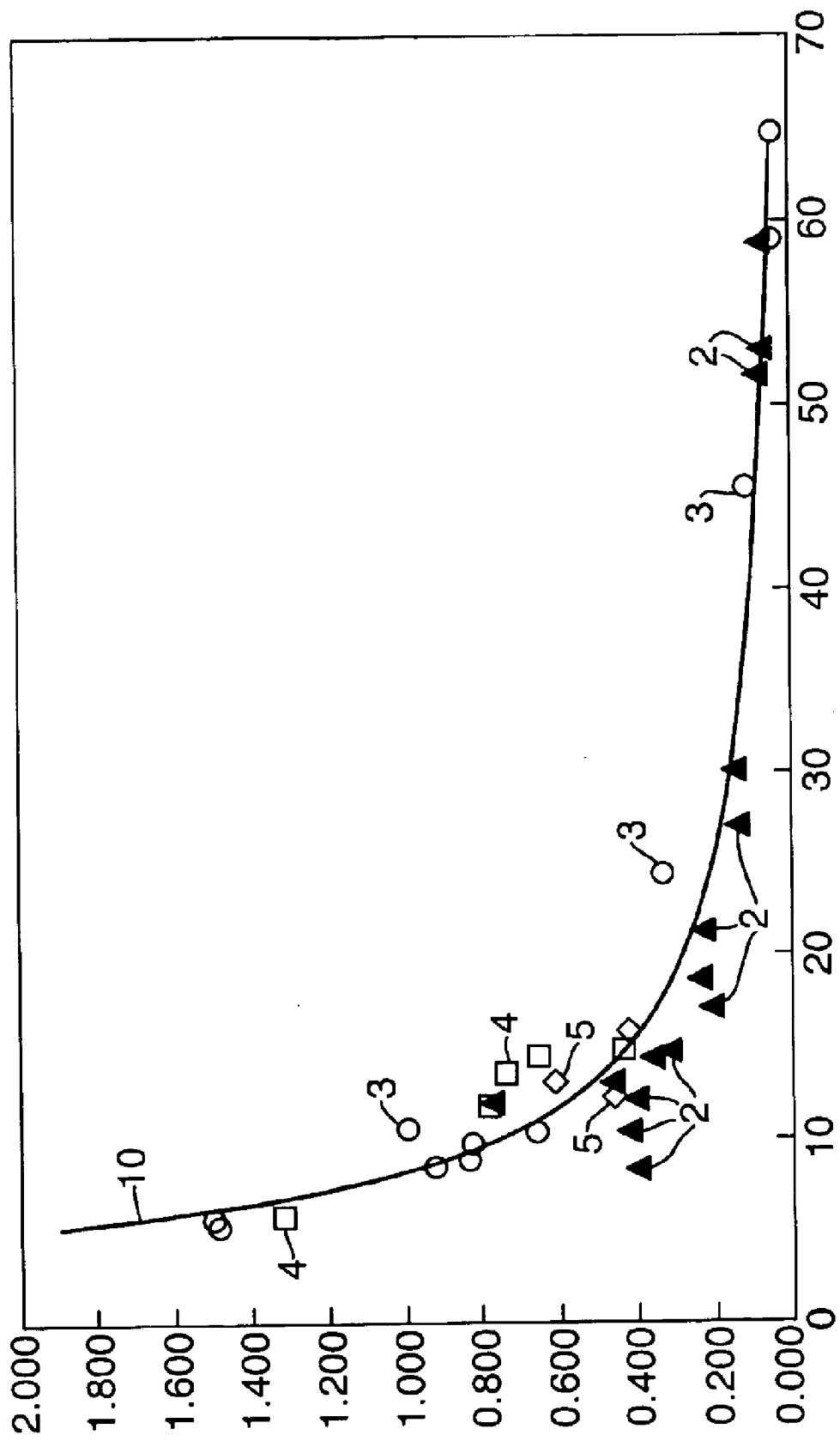
FIG. 2 shows the viscosity in centipoise (at in situ pressure and temperature) on the y-axis as a function of the crude oil property on the x-axis in arbitrary units.

The curve 10 shown in FIG. 2 shows the empirical relation that fits the data points 2, 3, 4 and 5 obtained from samples taken from reservoirs in the same geological area. The equation of the curve 10 is Visc=(19.8)(COP)$^{-1.4}$, with a goodness of fit $R^2$ of 0.96. The crude oil property, COP, had been determined by dividing the hydrocarbon oil property, COP, by the optical density of the oil peak.

Suitably the optical density of the oil peak is corrected by subtracting from it the base-line optical density.

In case the hydrocarbon reservoir fluid is a so-called heavy oil that is relatively viscous, it will be difficult to acquire a representative sample of the reservoir fluid. In order to obtain a representative sample, the step of making an exclusive fluid communication further includes activating a heating device arranged near the probe to heat the formation fluid.

Suitably, the probe is associated with a packer pad in an assembly, and the heating device is placed in the packer pad. Alternatively the heating device is arranged on the tool. The heating device may be a device generating microwaves, light waves or infrared waves. The heating device may also be an electrical heater, a chemical heater or a nuclear heater.

In the above the borehole traversing through the formation was not cased, and the exclusive fluid communication was formed by a probe extending into the formation. In case the borehole traversing the formation is cased, the exclusive fluid communication must be made in a different way. Thereto, the step of lowering in the borehole to the location a tool that comprises a central conduit having an inlet, means for displacing fluids through the central conduit, and an optical fluid analyser now comprises 1) making a perforation set through the casing wall into the formation at a location where the communication needs to be established;
2) lowering the tool into the borehole to the perforation set, which tool is further provided with an upper and a lower packer arranged at either side of the inlet of the central conduit, wherein the central conduit opens below the lower packer or above the upper packer, and wherein the distance between the upper and the lower packer is larger than the height of a perforation set, and wherein the step of making an exclusive fluid communication comprises setting the packers so that the perforation set is straddled between the packers.

Figure 3:
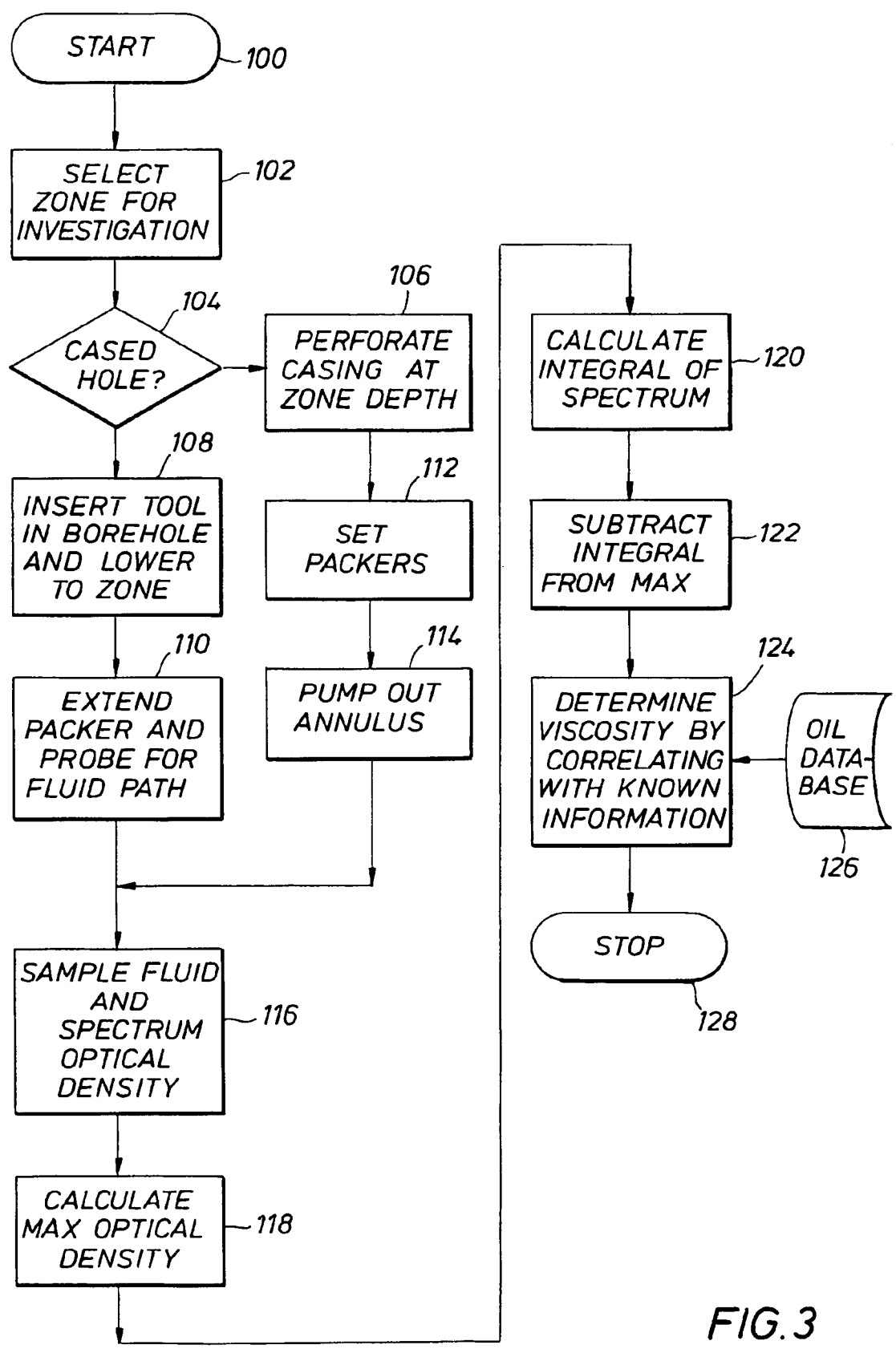
FIG. 3 is a flow chart showing the method of practicing the present invention.

FIG. 3 is a flow chart showing the method of the present invention. Beginning at step 100, the method proceeds to step 102, wherein the operator determines the zone and depth to be investigated. The operator further determines if the zone of investigation is a cased or open hole section in step 104. If an open hole, the formation test tool is inserted into the borehole and lowered to the selected zone in step 108. The tool packer and snorkel are then extended into the formation at the zone to establish exclusive fluid communication in step 110.

If the borehole is cased, it must first be perforated in step 106. This may be achieved utilizing known perforating methods, such as wireline or tubing conveyed guns. The tool is lowered to the desired zone and packers straddling the perforations are set in step 112. This effectively isolates the annulus in between the packers. The annulus is then pumped out through the central conduit in step 114.

Fluid samples are induced to flow into the tool where it is sampled and the spectrum fluid density is determined in step 116. In step 118 the maximum optical density is determined for a short wavelength multiplied with the length of the short wavelength range. In step 120, the second factor is calculated by as the integral over the same short-wavelength range of the spectrum. The process proceeds to step 122 in which the second factor is subtracted from the first. In step 124, the information determined in step 122 is fitted to a known oil properties from a database 126, to determine the best fit and the oil viscosity. The process then terminates at step 128.

What is claimed is:

1. A method of determining the viscosity of a hydrocarbon reservoir fluid that is present in a formation layer traversed by a borehole, said method comprises the steps of:
   a) selecting a location in the formation layer;
   b) lowering in the borehole to the location a tool that comprises a central conduit having an inlet, means for displacing fluids through the central conduit, and an optical fluid analyzer;
   c) making an exclusive fluid communication between the formation and the inlet of the central conduit;
   d) obtaining a spectrum of the optical density;
   e) calculating a first factor that is the maximum optical density in a predetermined short-wavelength range multiplied with the length of the short-wavelength range, calculating a second factor which is the integral over the same short-wavelength range of the spectrum, subtracting the second factor from the first factor to obtain a hydrocarbon oil property; and f) obtaining the magnitude of the in-situ viscosity from the oil property using a relation that had been obtained by fitting a curve through previously obtained data points comprising the measured magnitude of the actual viscosity as a function of the oil property.

2. The method according to claim 1, wherein the difference in step e) is divided by the optical density of the oil peak to obtain a crude oil property.

3. The method according to claim 2, wherein the optical density of the oil peak is corrected by subtracting from it the base-line optical density.

4. The method according to claim 1, wherein making an exclusive fluid communication between the formation and the inlet of the central conduit comprises extending into the formation a probe having an outlet that is in direct fluid communication with the inlet of the central conduit of the tool.

5. The method according to claim 4, wherein making an exclusive fluid communication further includes activating a heating device arranged near the probe to heat the formation fluid.

6. The method according to claim 1, wherein the formation is traversed by a cased borehole, wherein step b) comprises:

b1) making a perforation set through the casing wall into the formation at a location where the communication needs to be established;

b2) lowering the tool into the borehole to the perforation set, which tool is further provided with an upper and a lower packer arranged at either side of the inlet of the central conduit, wherein the central conduit opens below the lower packer or above the upper packer, and wherein the distance between the upper and the lower packer is larger than the height of a perforation set, and wherein step c) comprises setting the packers so that the perforation set is straddled between the packers.

* * * * *